United States Patent [19]

Peart et al.

[11] 4,380,763

[45] Apr. 19, 1983

[54] CORROSION MONITORING SYSTEM

[75] Inventors: Leland L. Peart, Sedona, Ariz.; John Farrar, Santa Ana, Calif.

[73] Assignee: The United States of America as represented by the Secretary of the Air Force, Washington, D.C.

[21] Appl. No.: 222,845

[22] Filed: Jan. 6, 1981

[51] Int. Cl.³ .................... G01N 27/46; G08G 19/16
[52] U.S. Cl. ......................... 340/870.16; 324/65 CR
[58] Field of Search ............ 324/65 R, 65 CR, 71 R, 324/451; 340/799, 870.16, 870.01, 870.27

[56] References Cited

U.S. PATENT DOCUMENTS

| | | | |
|---|---|---|---|
| 2,824,283 | 2/1958 | Ellison | 324/65 CR |
| 2,834,858 | 5/1958 | Schaschl | 201/63 |
| 3,047,847 | 7/1962 | Marsh et al. | 324/65 CR |
| 3,549,993 | 12/1970 | Marsh et al. | 324/71 |
| 3,631,338 | 12/1971 | Fitzpatrick et al. | 324/71 R |
| 4,208,264 | 6/1980 | Polák et al. | 324/65 CR |
| 4,262,292 | 4/1981 | Duley | 340/799 |
| 4,313,114 | 1/1982 | Lee et al. | 340/870.16 |

Primary Examiner—Thomas A. Robinson
Attorney, Agent, or Firm—Donald J. Singer; Frank J. Lamattina

[57] ABSTRACT

A system for detecting and measuring corrosive reaction of metals in an environment. The system includes: a remotely placeable sensor head containing a galvanic couple made of metals identical to those involved in the corrosion problem, with the couple coiled in the shape of a sprial; and, operatively associated electronic circuitry to amplify, integrate, and store in a non-volatile memory, e.g., a bubble type memory, for future recall the amount of galvanic current that is flowing and that has flowed when corrosion is, or has been, occurring.

6 Claims, 7 Drawing Figures

CORROSION MONITORING SYSTEM

STATEMENT OF GOVERNMENT INTEREST

The invention described herein may be manufactured and used by or for the Government for governmental purposes without the payment of any royalty thereon.

BACKGROUND OF THE INVENTION

This invention relates to corrosion monitoring and measurement and, more particularly, to system for detecting galvanic corrosion in an environment, and for amplifying, integrating and storing in a memory for future recall the amount and/or the rate of galvanic current that is flowing (and that has flowed) when galvanic corrosion is being (and has been) detected.

The visual inspection for corrosion of an item (or of a constituent component thereof) by personnel is subjective, can be time consuming and, therefore, expensive and ineffectual, depending upon the configuration of the item, its location and/or positioning, and the expertise of the inspecting personnel. For example, in an aircraft or an aircraft system there are many places where items (hereinafter referred to as "hardware") are corroding or are apt to corrode, and to which said places inspecting personnel cannot readily gain access. These places are, for all practical purposes, inaccessible routinely and can make inspection of an item therein for corrosion extremely difficult, if not impossible.

The results of undetected corrosion, or of detecting corrosion too late, can be the destruction of hardware which then requires replacement that, in turn, can be costly, because of the labor involved, the cost of the hardware to be replaced, and in some cases the loss of use of the equipment of which the corroded hardware is a necessary constituent. In addition, undetected corrosion processes may lead to, or actually cause, dangerous situations.

Therefore, what is needed in the art and is not presently available, is some means for detecting corrosion, and for objectively measuring the amount and rate of the corrosion, of hardware that is otherwise very difficult or impossible to inspect visually, so that timely corrective action can be taken to prolong the life of, rather than to replace, the corroding hardware.

We have invented such a means in the form of a corrosion monitoring system which has a remotely positionable sensor; and, thereby, we have advanced the state-of-the-art.

SUMMARY OF THE INVENTION

The corrosion process requires moisture. Accordingly, our inventive corrosion monitor system requires moisture to operate. In this regard, what is to be noted and is to be appreciated is that the amount of moisture usually in ambient air is sufficient to initiate and continue the corrosion process. However, very little corrosion occurs on metals below 60 percent relative humidity.

Our inventive corrosion monitor system detects and measures corrosion current which is in proportion, in accordance with Faraday's law, to the amount of metal consumed in the corrosion reaction.

The inventive system includes a remote sensor head device (hereinafter referred to as a "sensor") containing a galvanic couple which is representative of the corrosion problem being experienced. The galvanic current flowing when corrosive conditions are experienced is then amplified, integrated, and stored in a memory for future recall and display.

Additionally, if desired or deemed necessary, the monitoring system can include a visual and/or audio alarm which is triggered when the corrosion exposure exceeds a predetermined limit.

Accordingly, the principal object of this invention is to provide means for detecting and monitoring, accurately and reliably, the corrosion process of remotely located or inaccessible hardware, with said means capable of doing so rapidly and economically and without the user having any special technical skills.

Another object of this invention is to integrate the corrosion rate over time, so that one can read out the total extent of corrosion that has occurred.

Still another object of this invention is to provide a corrosion monitor system which can be adapted for a particular use. For example, although any galvanic couple component (e.g., an aluminum-copper one) will detect and monitor a corrosive environment (e.g., moisture or acids in the atmosphere), a specific galvanic couple component (i.e., a "tailor-made" couple) can be structured to detect and monitor corrosion in a particularly configured piece of hardware, or assembly, or system, or the like, which is in a particular environment.

Yet another object of this invention is to provide a corrosion monitoring system which can be used also in fluids (e.g., Freon) as well as in air environment.

These objects of this invention, as well as other related objects of this invention, will become readily apparent after a consideration of the description of the invention, together with reference to the Figures of the drawing.

DETAILED DESCRIPTION OF THE INVENTION

Figure 1:
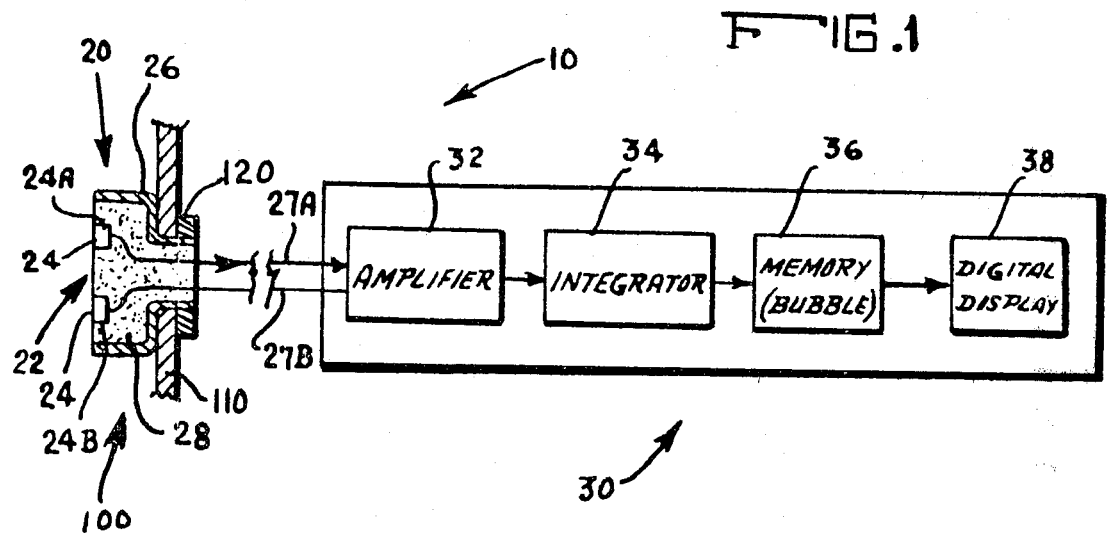
FIG. 1 is a simplified representation, in pictorial and schematic form of a preferred embodiment of the invention in which a single remotely located sensor is used.

With reference to FIG. 1, therein is shown a preferred embodiment 10 of this invention.

In the most basic and generic structural form, the invention corrosion monitoring system 10 (as shown by the embodiment in FIG. 1), comprises: (a) a means (generally designated 20) for sensing galvanic corrosion, with this means 20 disposed in an environment 100 wherein galvanic corrosion of preselected metals (such as representative ones 110 and 120) is to be monitored, such that if and when galvanic corrosion is sensed, an amount of galvanic current (as indicated by the arrow heads pointing away from this means 20) flows from the means 20; and (b) means (generally designated 30), in electrical connection with the galvanic corrosion sensing means 20, for amplifying, integrating, and storing in a non-volatile memory for recalling and displaying the amount of galvanic current that is flowing and that already has flowed from the galvanic corrosion sensing means 20.

As represented by the fragmentation of the leads in FIG. 1, the galvanic sensing means 20 is located remotely from the means 30. It is here to be noted that the means 20 can be located nearby, but is more useful either located remotely or located in a place or environment that in the usual and normal course of events is either inaccessible or, so difficult to gain access to, that it is inaccessible for all practical purposes, as will be shown later herein.

With reference to means 30, FIG. 1, and as indicated by the legends and by the electrical flow path designated by the arrow heads therebetween, this means 30 includes: (a) an amplifier means 32 in electrical connection with the galvanic sensing means 20; (b) an integrator means 34 in electrical connection with the amplifier means 32; (c) a non-volatile memory means 36 (such as a bubble memory) in electrical connection with the integrator means 34; and (d) a digital display means 38 in electrical connection with the non-volatile memory means 36. It is here to be noted that the non-volatile memory means 36 is preferred because it will prevent data loss in the event of power failure.

Figure 3A:
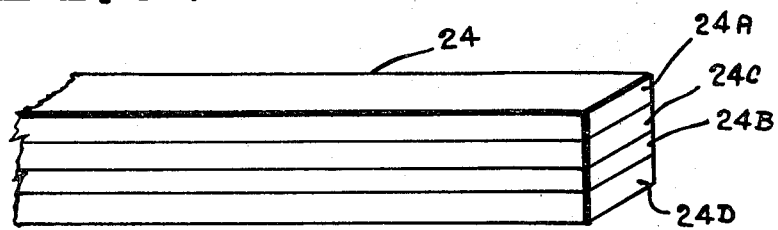
FIGS. 3A-3D, inclusive, show in simplified schematic form, a representative galvanic couple sensor that is a component of the invention, and also show some of the various steps in its structuring.
Figure 3B:
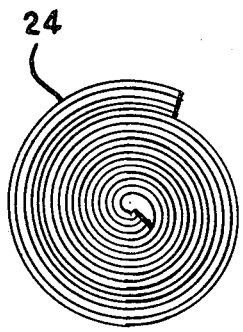
Figure 3C:
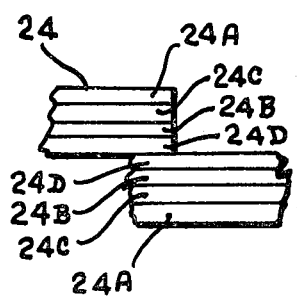
Figure 3D:
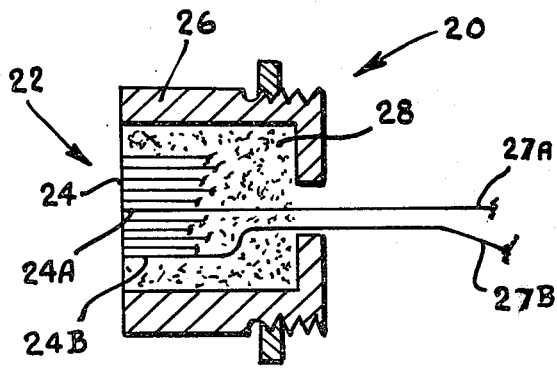

With reference now to FIG. 1 and FIGS. 3A-3D, inclusive, the galvanic corrosion sensing means 20, FIGS. 1 and 3D, includes a sensor (head device) 22 which further includes a galvanic couple 24 made of metals (such as 24A and 24B) that are identical to the preselected metals (such as 110 and 120, FIG. 1) which are to be monitored for galvanic corrosion. The galvanic couple 24 is preferably coiled in the shape of a spiral (as is emphasized in FIG. 3B) and is potted in a housing 26 that is made of electrically insulating material (such as any of the readily available moldable plastics), with the leads (such as 27A and 27B, FIGS. 1 and 3D) protruding therefrom.

As a matter of preference and not of limitation, and for illustrative purposes, some of the various structural steps of constructing the sensor 22 are shown in FIGS. 3A-3D, inclusive. Firstly, strips of the two dissimilar (i.e., different) metals (such as 24A and 24B) that are identical to the preselected metals (e.g., metal 24A is identical to metal 110, FIG. 1, and metal 24B is identical to metal 120, FIG. 1) are laminated in layered position, as best shown in FIG. 3A, with conventional insulating-/bonding materials (such as 24C and 24D, FIG. 3A), such that a multiple-layered strip is formed. Then, the multiple-layered strip is rolled into a spiral coil, as best shown in FIG. 3B, with the lowest layer (i.e., insulating/bonding material 24D) bonded to the uppermost layer (i.e., metal 24A), as best shown in FIGS. 3B and 3C. Next, insulated conductor leads 27A and 27B are attached to, respectively, metals 24A and 24B. Then, the coil assembly (which includes metals 24A and 24B, insulating/bonding materials 24C and 24D, and portions of leads 27A and 27B) is inserted into the moldable plastic housing 26 which has been molded into the desired and/or needed shape. Lastly, the coil assembly is potted in the housing 26 with suitable conventional potting compound 28. The sensor 22 is thereby formed.

Figure 2:
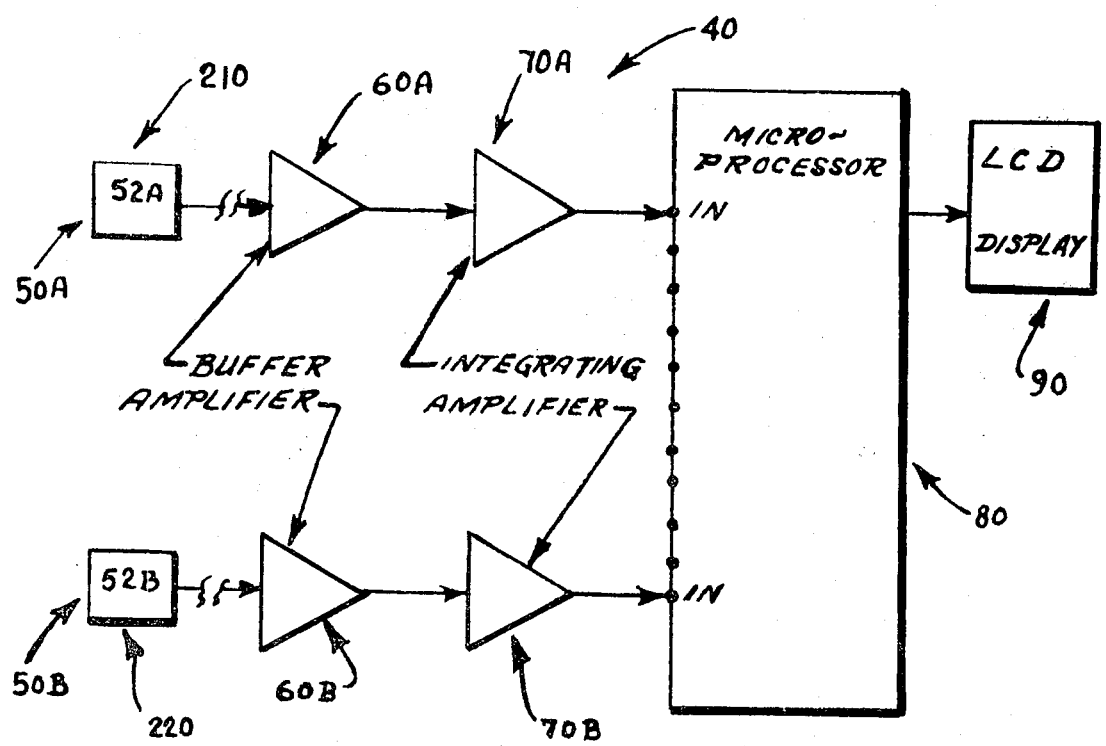
FIG. 2 is a simplified representation, in schematic form, of the preferred embodiment of a variation of the invention in which a plurality of remotely located sensors (i.e., one sensor for each different environment or the like) are used.

With reference to FIG. 2, therein is shown, in simplified schematic form, a preferred embodiment 40 of a variation of the invention, in which said variation a plurality of remotely located sensors, such as 52A and 52B, which are similar in structure to the previously described and shown sensor 22, FIGS. 1 and 3A-3D, inclusive, are used to sense corrosion conditions in different environments (or of different pieces of hardware, or in different places in the same environment, or in different locations on the same hardware), with said environments, or the like, being generally designated, respectively, 210 and 220 for identification purposes.

This variation 40 comprises, in its most basic form, the following components: (a) a plurality of means (such as 50A and 50B) for sensing galvanic corrosion that are disposed in a plurality of environments or the like (such as the aforementioned ones 210 and 220) in which galvanic corrosion of preselected materials is to be monitored, with at least one of these means disposed in at least each of the environments (e.g., means 50A is disposed in environment 210); (b) a plurality of buffer amplifier means (such as 60A and 60B), with each means of this plurality in electrical connection with a different one of the plurality of means for sensing galvanic corrosion (e.g., means 60A is connected to means 50A); (c) a plurality of integrating amplifier means (such as 70A and 70B), with each means of this plurality in electrical connection with a different one of the plurality of buffer amplifier means (e.g., means 70B is connected to means 60B); (d) a microprocessor (such as 80), which receives and stores the amplified and integrated input, in electrical connection with the plurality of integrating amplifier means (e.g., means 80 is connected to means 70A and to means 70B); and (e) a readout display means (such as 90), preferably of the LCD type, in electrical connection with the microprocessor.

As was the situation in the preferred embodiment 10, FIG. 1, each galvanic corrosion sensing means 50A and 50B of this variation 40 in FIG. 2 includes a sensor, such as 52A and 52B, and each sensor further includes a galvanic couple which is similar to or is identical to the already described and shown galvanic couple 24 of FIG. 3, i.e., each galvanic couple is made of metals identical to the preselected metals that are to be monitored for galvanic corrosion, and is coiled in the shape of a spiral, and also is potted in a housing of electrically insulated material that preferably is made of moldable plastic which has been molded to the desired or needed shape.

Also, as was the situation with regard to the preferred embodiment 10, FIG. 1, the galvanic sensing means 50A and 50B are remotely located from their respective buffer amplifier means 60A and 60B, as is schematically represented by the broken lead lines.

Figure 4:
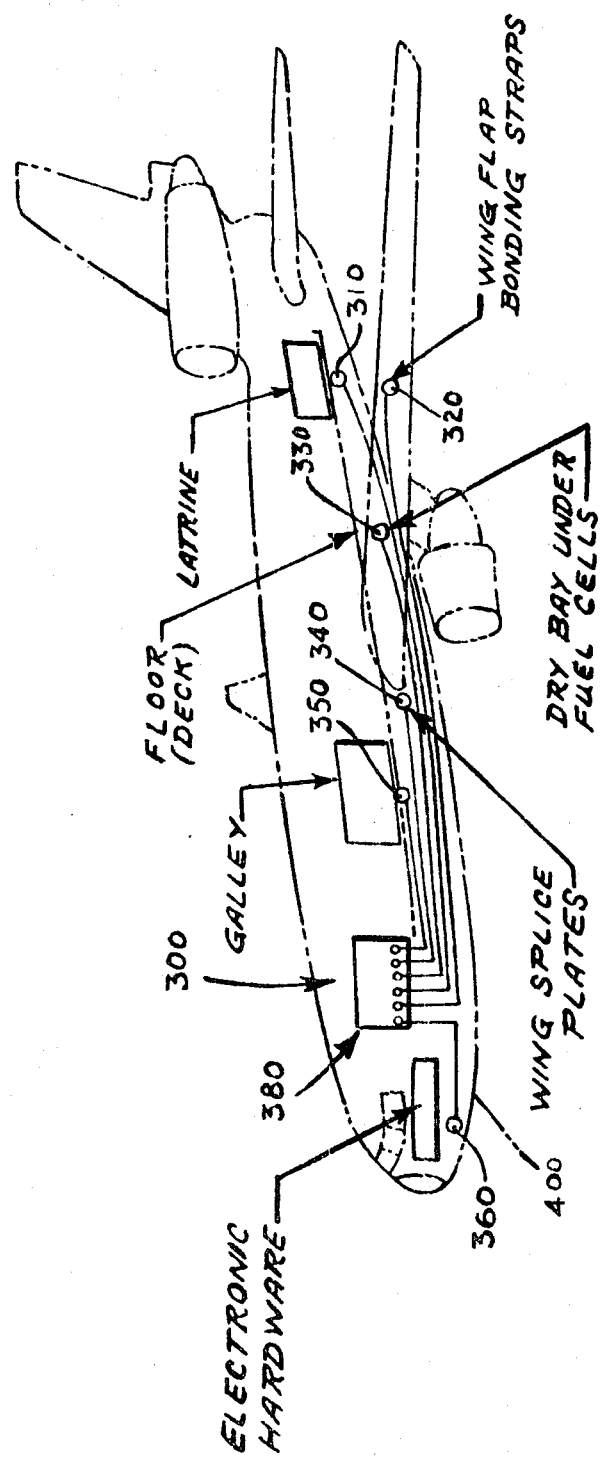
FIG. 4 shows, in pictorial and simplified schematic form, the multiple sensor embodiment of the invention (shown in FIG. 2) in a representative application, i.e., in use in and on an aircraft.

Now, with reference to FIG. 4, therein is shown, in pictorial and simple schematic form, a multiple sensor variation 300 of our inventive corrosion monitoring system in a represenative application, i.e., in use on and in an aircraft 400. To better orient the reader, with regard to accessibility, the "floor" (i.e., the deck) of the aircraft 400 is shown and legended.

In an aircraft, such as 400, there are a multiplicity of locations (i.e., environments) where, for many reasons, a corrosion process can begin and continue. Some of these locations are the latrine, the wing flap bond straps area, the dry bay under the fuel cells, the wing splice plate area, the galley, and the area under and/or behind the flight panel electronics. These representative areas are identified in FIG. 4 by an arrow together with an appropriate legend. If each of these six (6) locations is to be monitored for corrosion with our inventive system 300, FIG. 4, then at least six (6) of our galvanic corrosion sensing means (such as 310-360, inclusive, FIG. 4) will be needed, i.e., one sensing means for each location to be monitored. It is here to be remembered that all of our galvanic corrosion sensing means (such as 20, FIGS. 1 and 3; and 210 and 220, FIG. 2; and also 310-360, inclusive, FIG. 4) are similar, and that each includes our sensor 22, FIGS. 1 and 3D, in turn, includes our galvanic couple 24, FIGS. 1 and 3D.

In FIG. 4 the "electronics," i.e., the means for amplifying, integrating, and storing in a non-volatile memory for recalling and displaying the amount of galvanic current that is, and has been, flowing is generally designated 380, and the six remotely located sensors 310-360, inclusive, are shown in position and in electrical connection with the means 380.

MANNER OF OPERATION AND OF USE OF THE INVENTION

The manner of operation and of use of the inventive corrosion monitoring system (such as 10, FIG. 1; 40, FIG. 2; and 300, FIG. 4) can be easily ascertained by any person of ordinary skill in the art from the foregoing description, coupled with reference to the contents of the Figures of the drawing.

For others, it is sufficient to say in explanation that the operation and use of our inventive corrosion monitoring system is based upon two scientific facts, namely: (a) that corrosion of a metal consists of the slow chemical and electrochemical reactions between the metal and the moisture of the environment in which the metal is located; and (b) that, if two different metals are in contact with an electrolyte (e.g., the moisture of the environment) and therefore are, in effect, in contact with each other, then a closed circuit results with an electric potential between the metals, and corrosion of one of the metals takes place. In this regard it is to be noted that, as a practical matter, a metal (such as aluminum) used in a particular application (such as is used in making an aircraft) is an alloy of the metal, rather than the metal in pure form. In that situation, two or more metals (rather than one) would be involved.

Accordingly, if the hardware to be monitored for corrosion is made of two different metals, then the galvanic couple 24 is made of the two metals. If the hardware is made of more than two different metals, then the couple 24 can be made of any two of the metals involved. If the hardware is of only one metal, then the couple 24 is made of that metal plus any other metal, e.g., copper. If an environment only is involved, i.e., no hardware is involved, then the couple 24 can be made of any two different metals (e.g., aluminum and copper).

CONCLUSION

It is abundantly clear from all of the foregoing, and from the Figures of the drawing, that the stated desired object of this invention, as well as other related objects of this invention, have been achieved.

It is to be noted that, although there have been described and shown the fundamental and unique features of this invention as applied to a preferred embodiment 10, FIG. 1, and a variation thereof 40, FIG. 2, and also a representative use thereof in FIG. 4, that various other embodiments, variations, adaptations, substitutions, additions, omissions, and the like may occur to, and can be made by, those of ordinary skill in the art, without departing from the spirit of the invention. For example: (a) the invention can be provided with a visual and/or audio alarm which is activated automatically when the corrosion exposure exceeds either an incremented, or a cumulative, predetermined limit; (b) the thickness and length of the metals used in the galvanic couple 24, and the insulation composition and thickness, can be varied to enhance the performance of the sensor 22; and (c) the overall shape of the sensor 22 can be modified to be useable in specific applications.

What is claimed is:

1. A corrosion monitoring system, comprising:
   a. means for sensing galvanic corrosion, with said means disposed in an environment where galvanic corrosion of preselected metals is to be monitored, whereby when galvanic corrosion is sensed an amount of galvanic current flows from said means, wherein said means includes a sensor head device which further includes a galvanic couple made of metals identical to said preselected metals to be monitored for galvanic conversion, with said couple coiled in the shape of a spiral and potted in a housing made of electrically insulating material; and
   b. means, in electrical connection with said galvanic corrosion sensing means, for amplifying, integrating, and storing in a non-volatile memory for recalling and displaying said amount of galvanic current that is flowing and has flowed from said galvanic corrosion sensing means, wherein said amplifying, integrating, and storing means includes:
      (1) amplifier means in electrical connection with said galvanic corrosion sensing means;
      (1) integrator means in electrical connection with said amplifier means;
      (3) non-volatile memory means in electrical connection with said integrator means, wherein this means includes a bubble memory component; and
      (4) digital display means in electrical connection with said non-volatile memory means.

2. A corrosion monitoring system, as set forth in claim 1, wherein said galvanic corrosion sensing means is located remotely from said means for amplifying, integrating, and storing said amount of galvanic current from said galvanic corrosion sensing means.

3. A corrosion monitoring system, comprising the following components:
   a. a plurality of means for sensing galvanic corrosion disposed in a plurality of environments where galvanic corrosion of preselected materials is to be monitored, with at least one of said means disposed in at least each one of said environments, and wherein each of said plurality of these means includes a sensor head device which further includes a galvanic couple made of metals identical to said preselected metals to be monitored for galvanic corrosion, with said couple coiled in the shape of a spiral, and with said spiral coiled galvanic couple potted in a housing of electrically insulating material;
   b. a plurality of buffer amplifier means, with each means of this plurality of means in electrical connection with a different one of said plurality of means for sensing galvanic corrosion;
   c. a plurality of integrating means, with each means of this plurality of means in electrical connection with a different one of said plurality of buffer amplifier means;

d. a microprocessor in electrical connection with said plurality of integrating amplifier means, and e. a readout display means in electrical connection with said microprocessor.

4. A corrosion monitoring system, as set forth in claim 3, wherein each of said plurality of means for sensing galvanic corrosion is located remotely from said other components of said system.

5. A corrosion monitoring system, comprising:

a. means for sensing corrosion, wherein said means includes a sensor head device which further includes a galvanic couple made of any two different preselected metals, with said couple coiled in the shape of a spiral, and with said means disposed in an environment to be tested for corrosiveness, whereby when corrosion is sensed, an amount of galvanic current flows from said means; and b. means, in electrical connection with and remotely located from said corrosion sensing means, for amplifying, integrating, and storing in a non-volatile memory for recalling and displaying said amount of galvanic current that is flowing and that has flowed from said corrosion sensing means.

6. A corrosion monitoring system, as set forth in claim 5, wherein said two different preselected metals are aluminum and copper.

* * * * *